(12) United States Patent
Rankins

(10) Patent No.: US 6,520,909 B1
(45) Date of Patent: Feb. 18, 2003

(54) ADJUSTABLE TONGUE BLADE HOLDER FOR ENDOSCOPE

(76) Inventor: Robert C. Rankins, 2700 Brookside, McKinney, TX (US) 75070-4212

( * ) Notice: Subject to any disclaimer, the term of this patent is extended or adjusted under 35 U.S.C. 154(b) by 0 days.

(21) Appl. No.: 09/572,708

(22) Filed: May 16, 2000

(51) Int. Cl.⁷ ............................................... A61B 1/267
(52) U.S. Cl. ..................... 600/196; 600/200; 600/193; 600/240; 600/241
(58) Field of Search ........................... 600/200, 240, 600/241, 235, 237, 238, 239, 197, 199, 193, 127, 104, 196

(56) References Cited

U.S. PATENT DOCUMENTS

| | | | |
|---|---|---|---|
| 1,510,304 A | * | 9/1924 | Cameron ..................... 600/241 |
| 1,666,265 A | | 4/1928 | Rosenfeld |
| 1,908,010 A | | 5/1933 | Cameron |
| 1,990,972 A | * | 2/1935 | Arnesen ..................... 600/200 |
| 2,023,945 A | | 12/1935 | Allyn ............................. 128/9 |
| 2,646,036 A | * | 7/1953 | Allyn et al. ................. 600/193 |
| 2,646,037 A | * | 7/1953 | Cook et al. ................. 600/196 |
| 2,649,087 A | * | 8/1953 | Allyn et al. ................. 600/193 |
| 2,678,645 A | * | 5/1954 | Raimo ........................ 600/200 |
| 3,153,267 A | | 10/1964 | Rowland, Jr. |
| 3,760,798 A | | 9/1973 | Edinger |
| 3,848,587 A | * | 11/1974 | McDonald .................. 600/187 |
| 4,320,745 A | * | 3/1982 | Bhitiyakul et al. ......... 600/138 |
| 5,891,019 A | * | 4/1999 | Young et al. ............... 600/240 |
| 5,897,492 A | * | 4/1999 | Feller et al. ................ 600/240 |

* cited by examiner

Primary Examiner—Linda C. M. Dvorak
Assistant Examiner—Jocelyn Ram
(74) Attorney, Agent, or Firm—Crutsinger & Booth

(57) ABSTRACT

The present invention contemplates a new device for adjustably attaching a tongue blade to an endoscope. In general, the device secures a tongue blade holder to the body of an endoscope and permits adjustment of the angle of the tongue blade with respect to the light source of the endoscope. Typically, the device has a clamp for receiving an endoscope body near the juncture of the handle and the light source of the endoscope. The clamp has a fastener for securing the clamp to the outer surface of the endoscope body and may be adapted for use with endoscopes somewhat larger or smaller in cross section than the clamp opening. The clamp has an attached tongue blade holder pivotably attached to the clamp and securable at an angle relative to the endoscope light source. The device also has several surfaces for the display of graphics.

14 Claims, 2 Drawing Sheets

ADJUSTABLE TONGUE BLADE HOLDER FOR ENDOSCOPE

TECHNICAL FIELD

This invention relates to a new device for securing a tongue blade to an endoscope. The device allows adjustment of the tongue blade to a desired angle relative to the light source of the endoscope.

BACKGROUND OF THE INVENTION

An endoscope is commonly used for medical examinations, particularly of the ears, nose and throat. In examining the throat, medical practitioners often also employ a tongue blade for pressing on the tongue or adjusting the angle of the jaw of the patient. Despite the simplicity and effectiveness of these two tools, the examination is often hampered by the disadvantageous fact that the medical practitioner is typically limited by having one of the tools in each hand. This can be a serious problem in situations where it would be advantageous for the medical practitioner to grasp or manipulate an additional object. It is also a serious problem for the medical practitioner to have both hands occupied when attempting to examine the throat of a patient who is unable or unwilling to hold still, as is often the case with children, for example. A few attempts have been made to address these problems, but the they have not been entirely satisfactory.

A lighted diagnostic instrument with a carrier for securing a tongue depressor is disclosed in U.S. Pat. No. 1,990,972 to Arneson. However, this apparatus has the problem of eliminating the possibility of varying the angle between the instrument eyepiece and the tongue depressor, as can be done with the two-handed examination method. Thus, the tool does not provide an advantageous viewing angle for examining patients of proportions that do not correspond to those of the tool. Obviously, this is a serious limitation on the usefulness of the apparatus. Additionally, there is no surface suitable for affixing graphics, which is a commercial disadvantage. Also, the apparatus of this design is constructed as a combined unit consisting of a particular endoscope with a carrier, not as a device for possible use with various endoscopes.

The apparatus of U.S. Pat. No. 1,510,304 to Cameron, discloses another attempt to provide useful illumination to a tongue depressor. As with the previously cited design, this apparatus provides only one viewing angle parallel with the light source. Again, this apparatus is also a combined unit of a particular endoscope with an attached receiving member. Also, this device has no surface adapted for the display of graphics.

U.S. Pat. No. 2,023,945 to Allyn discloses another combination light holder and spatula holder unit. This apparatus has the same disadvantages in common with the above-cited patents. The light source and spatula of this apparatus are pivotable as a unit, but the angle of the spatula relative to the light source is not adjustable. This device does not have any surfaces particularly adapted for displaying graphics.

SUMMARY OF THE INVENTION

The present invention contemplates a new device for adjustably attaching a tongue blade to an endoscope. In general, the device secures a tongue blade holder to the body of an endoscope in a way that permits adjustment of the angle of the tongue blade with respect to the light source of the endoscope.

The device for securing a tongue blade to an endoscope has a clamp attachable to an endoscope body. The clamp is affixed to a tongue blade holder via a joint fastenable at selectable angles relative to the endoscope light source.

According to one aspect of the invention, the fastenable joint incorporates corresponding ridge-and-groove surfaces providing a plurality of tongue blade holder angle adjustments.

According to another aspect of the invention, the fastenable joint is tightened with a thumb screw.

According to yet another aspect of the invention, the device provides surfaces adapted for the display of graphics.

According to still another aspect of the invention, the device includes one or more flexible sleeve sized to fit around the endoscope body and within the inner surface of the clamp for securing the clamp to an endoscope body of external dimensions smaller than the internal dimensions of the clamp.

According to yet an additional aspect of the invention the clamp for securing the device to the endoscope body is a split ring.

BRIEF DESCRIPTION OF THE DRAWINGS

The accompanying drawings are incorporated into and form a part of the specification to illustrate several examples of the present invention. These drawings together with the description serve to explain the principals of the invention. The drawings are only for the purpose of illustrating preferred and alternative examples of how the invention can be made and used and are not to be construed as limiting the inventions to only the illustrated and described examples. The various advantages and features of the present invention will be apparent from a consideration of the drawings in which.

DETAILED DESCRIPTION

Figure 1:
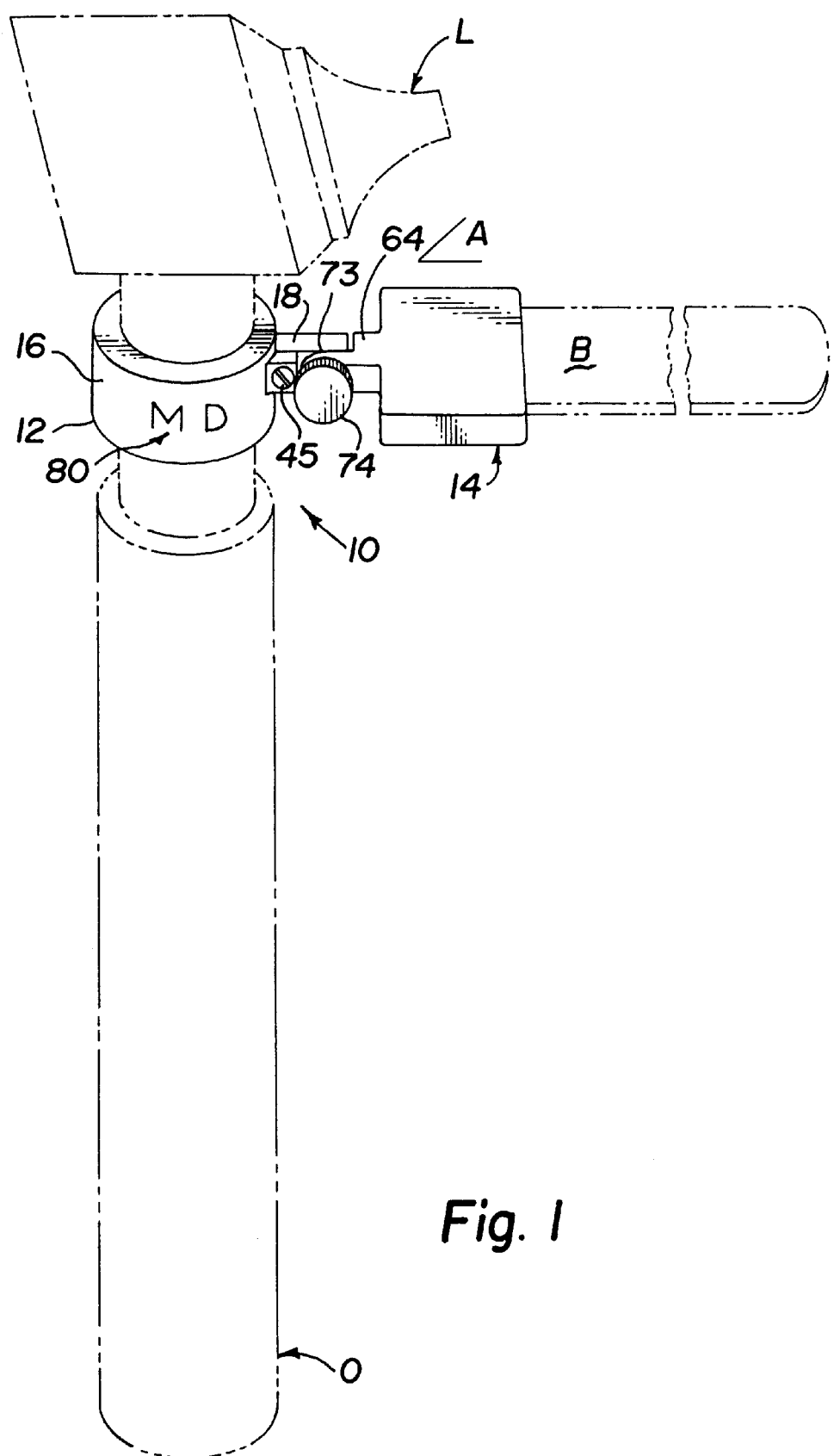
FIG. 1 is a top perspective view of the tongue blade holding device with an endoscope (not part of the invention)

Embodiments of the present inventions will be described by referring to drawings of the device and examples of how the inventions can be made and used. In these drawings reference characters are used throughout the several views to indicate like or corresponding parts.

In the description of the invention, certain terms are employed to refer to the parts and structures of the device. The term "endoscope" means an instrument for visually examining the inside of a body cavity accessible through a natural orifice. The term "tongue blade" is used to mean a wooden or plastic tongue depressor of the type well known in the art. The term "graphics" means visible markings and is intended to encompass all manner of printing, engraving, letters, characters, insignia, drawings, symbols, logos, trademarks, and the like.

FIGS. 1–4 illustrate a new device shown securing a tongue blade to a light source, for example, an endoscope. Referring primarily to FIG. 1, in general, the device 10 has a clamp portion 12 and a blade holder portion 14. The clamp portion 12 secures the device to an instrument such as, for a more specific example, an otoscope O. The tongue blade holder portion 14 holds a tongue blade B. Neither the otoscope O, nor the tongue blade B, are part of the invention. In the description of the invention, certain terms are employed to refer to the positional relationship of certain structures relative to other structures. In all figures, the term "longitudinal" means the direction defined by the axis of body of the otoscope O. Correspondingly, the term "transverse" means the direction perpendicular to the longitudinal axis. The terms "upper" or "top" and "lower" or "bottom," "front" and "rear," "vertical" and "horizontal." are used for convenience in reference to the orientations shown in the drawings and are not intended to be assignatory in the context of making and using the invention.

With reference to FIGS. 1–4, the device 10 for securing a tongue blade B to an endoscope is more fully described. The device is preferably made from rigid plastic but may also be made from metal or other rigid material. The clamp portion 12 of the device 10 has a split ring 16 for receiving the body of an instrument, and an integral transverse arm 18 extending radially. In this description, the instrument is an otoscope O with a substantially cylindrical body as is common in the art. Of course the invention may be practiced with otoscopes, as shown, or other instruments known in the arts. The split ring shown in this example could be a clamp made in any shape to substantially correspond to an existing endoscope body.

The split ring 16 defines a longitudinal hollow cylinder open at its top end 20 and bottom end 22. The split ring 16 has an inner surface 24 and an outer surface 26. The arm 18 is composed of two shanks: a short shank 28 and a long shank 30. The short shank 28 has an inner surface 32, and an outer surface 34. The long shank 30 also has an inner surface 36, and an outer surface 38. respectively. The shanks 28, 30, are adjacent at their respective inner surfaces 32, 36, and parallel to one another. The short shank has a terminal end 40, and the long shank has a terminal end 42. The arm 18 has a cylindrical fastener hole 44 extending through both shanks 28, 30, perpendicular to the transverse and longitudinal axes. Fastener hole 44 is threaded to accept a screw 45. The arm 18 also has a cylindrical attachment hole 46 through the long shank 30 perpendicular to the longitudinal and transverse axes. Attachment hole 46 is threaded to accept a threaded fastener. A plurality of ridges 48 on the inner surface 36 radiate around the attachment hole 46. It will be clear to those skilled in the arts that different types of fasteners may be used such as a bolt or a removable pin or rivet.

The tongue blade holder 14 preferably has a rectangular box-like outer shape with an upper surface 50 parallel to a lower surface 52, two opposing sides 54, 56, and a front 58 and a rear 60. The front 58 of the tongue blade holder 14 has a slot 62 of a size to receive a tongue blade B end lengthwise in a horizontal orientation. The slot 62 preferably has parallel opposing sides 61, 63, and a top 65 and bottom 67 slightly angled toward one another at the rear. The tongue blade holder 14 has an integral pivot arm 64 approximately perpendicular and centered at the rear 60. The pivot arm 64 has an outer surface 66 and an inner surface 68. The pivot arm 69 is rounded or shortened to permit the pivoting described below. The pivot arm 64 has a cylindrical pivot hole 70 corresponding to the size and orientation of the attachment hole 46 of the clamp 12. Grooves 72 on the inner surface 68 radiate from around the circumference of the pivot hole 70. The grooves 72 are sized to receive the ridges 48 of the inner surface 36 of the long shank 30 of the clamp 12. The grooves 72 and ridges 48 are designed to lock together in an interdigital manner forming a ridge-and-groove joint 73. A fastener, preferably a thumbscrew 74, is provided for passing through the pivot hole 70 and fastening with the threads of attachment hole 46. It should be understood that other types of adjustable joints and fasteners may be used to provide an adjustable yet securable joint.

Figure 2:
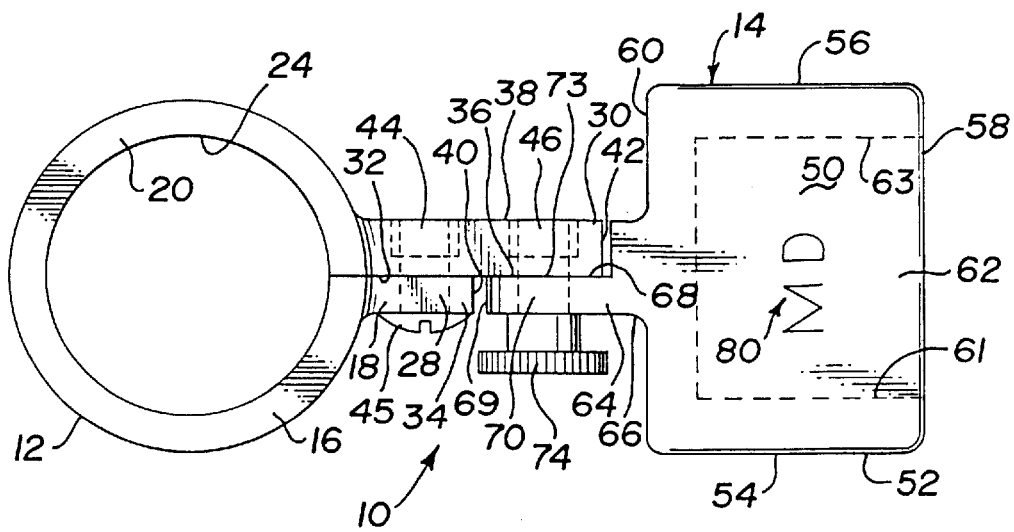
FIG. 2 is a top view of the tongue blade holding device of FIG. 1.
Figure 3:
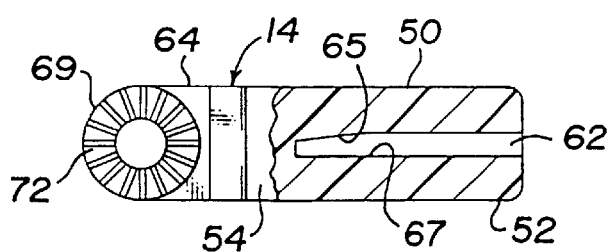
FIG. 3 is a side view of the tongue blade holding device of FIG. 1.
Figure 4:
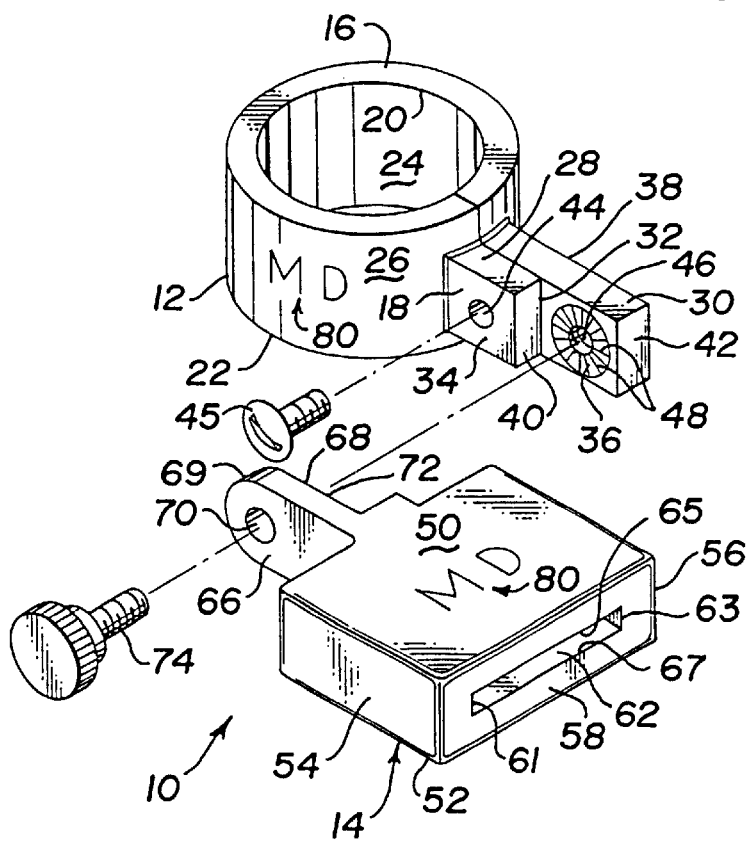
FIG. 4 is an exploded top perspective view of the tongue blade holding device of FIG. 1.

The use of the device 10 for securing a tongue blade to a light source L of the otoscope O is best seen in FIGS. 1 and 2. The split ring 16 of the clamp 12 is placed so that it encircles the body of an endoscope or other light source. In this case an otoscope O familiar in the art is shown. The screw 45 is tightened sufficiently to secure the split ring 16 to the otoscope O body without slipping. The pivot arm 64 is fastened to the arm 18 of the clamp 12 by a thumbscrew 74 inserted through pivot arm hole 70 and tightened into the threads in the attachment hole 46. When thumbscrew 74 is fully tightened, the pivot arm inner surface 68 contacts the inner surface 36 of long shank 30. The grooves 72 receive ridges 48, providing an interlocking ridge-and-groove joint 73 firmly securing the blade holder 14 to the clamp 12 at a desired angle A with respect to the light source L. Subsequent adjustments may be made by loosening the thumbscrew 74, pivoting the holder about the thumbscrew to a desired angle, and re-tightening the thumbscrew 74. A tongue blade B may be removed and replaced from the slot 62 as desired. A tongue blade is preferably held in place by pressure from the top 65 and bottom 67 of the slot, although other methods such as a leaf spring arrangement or set screw may also be used.

If an endoscope larger than the diameter of the split ring 16 is encountered, the split ring may nevertheless be fastened to the body of the endoscope as above. This will result in the inner surfaces 28, 36 of the shanks 28, 30 being held substantially parallel, but not touching, by threaded fastener 45, in this case, a screw. This aspect of the invention is best seen in FIG. 2. If an endoscope smaller in diameter than the diameter of the split ring 16 is to be used with the invention, one or more sleeves, preferably of flexible material such as flexible plastic or expanded plastic foam, may be inserted between the inner surface 24 of the split ring 16 and the endoscope body. As can be seen with reference to FIG. 4, tightening screw 45, then secures the split ring 16 and sleeve around the otoscope body O.

As shown in FIGS. 1–4, the invention includes several surfaces capable of displaying graphics 80. Namely, the external peripheral surface of the split ring 26, and the upper surface 50 and lower surface 52 of the holder 14. For example, these surfaces are advantageous for the display of logos, initials, trademarks, trade names, a particular physician's name, decorative design, or other graphic content.

The embodiments shown and described above are only exemplary. Many details are often found in the art such as variations in the size and shape of endoscopes or other light sources. Therefore many such details are neither shown nor described. It is not claimed that all of the details, parts, elements, or steps described and shown were invented herein. Even though numerous characteristics and advantages of the present inventions have been set forth in the foregoing description, together with details of the structure and function of the inventions, the disclosure is illustrative only, and changes may be made in the detail, especially in matters of shape, size and arrangement of the parts within the principles of the inventions to the full extent indicated by the broad general meaning of the terms used in the attached claims. For example, the placement of the interlocking grooves and ridges of the clamp/holder portions of the invention could be rearranged. Similarly, different materials could be used, or different types of fasteners or thumbscrews, all within the concept of the invention.

The restrictive description and drawings of the specific examples above do not point out what an infringement of this of this patent would be, but are to provide at least one explanation of how to make and use the inventions. The limits of the inventions and the bounds of the patent protection are measured by and defined in the following claims.

What is claimed is:

1. A device for securing a tongue blade to an endoscope having a light source, the device comprising:
    a clamp attachable to an endoscope body;
    a tongue blade holder;
    a joint affixing the tongue blade holder to the clamp at selectable angles relative to the endoscope light source; and
    a fastener for securing the joint at a selected angle.

2. A device for securing a tongue blade to an endoscope according to claim 1 wherein the joint further comprises:
    a ridge-and-groove joint providing a plurality of tongue blade holder angle adjustments.

3. A device for securing a tongue blade to an endoscope according to claim 1 further comprising:
    graphics on a periphery of the clamp.

4. A device for securing a tongue blade to an endoscope according to claim 1 further comprising:
    graphics on an upper surface of the tongue blade holder.

5. A device for securing a tongue blade to an endoscope according to claim 1 further comprising:
    graphics on a lower surface of the tongue blade holder.

6. A device for securing a tongue blade to an endoscope according to claim 1 wherein:
    the joint is fastenable by a thumbscrew and corresponding threads.

7. A device for securing a tongue blade to an endoscope having a light source, the device comprising:
    a clamp attachable to an endoscope body:
    a tongue blade holder;
    a joint affixing the tongue blade holder to the clamp at selectable angles relative to the endoscope light source; and
    a fastener for securing the joint at a selected angle;
    wherein the clamp further comprises:
        a split ring for receiving an endoscope body;
        two shanks extending from the split ring; and
        threaded holes in the shanks aligned to receive a correspondingly threaded screw fastener to secure the split ring to the endoscope body.

8. A device for securing a tongue blade to an endoscope according to claim 7 wherein the joint further comprises:
    interlocking ridges and grooves in the split ring and tongue blade holder radially surrounding the threaded holes providing a plurality of angle adjustments securable by a threaded fastener.

9. A device for securing a tongue blade to an endoscope according to claim 7 further comprising:
    graphics on a periphery of the split ring.

10. A device for securing a tongue blade to an endoscope according to claim 7 further comprising:
    graphics on an upper surface of the blade holder.

11. A device for securing a tongue blade to an endoscope according to claim 7 further comprising:
    graphics on a lower surface of the blade holder.

12. A device for securing a tongue blade to an endoscope comprising:
    a clamp for receiving an endoscope body;
    two shanks extending from the clamp;
    threaded holes in the shanks aligned to receive a correspondingly threaded screw fastener to secure the claim to the endoscope body;
    a tongue blade holder; and
    a fastenable ridge-and-groove joint affixing the tongue blade holder to one or more of the shanks wherein the tongue blade holder can be adjustable secured to the clamp with a corresponding thumbscrew.

13. A device for securing a tongue blade to an endoscope according to claim 12 wherein,
    the clamp comprises a split ring.

14. A device according to claim 12, further comprising:
    graphics on an outer surface at least one of the clamp or tongue blade holder.

* * * * *